United States Patent
Iizuka et al.

(10) Patent No.: US 7,125,983 B2
(45) Date of Patent: Oct. 24, 2006

(54) L-NUCLEIC ACID DERIVATIVES AND PROCESS FOR THE SYNTHESIS THEREOF

(75) Inventors: Hajime Iizuka, Mobara (JP); Kazuhiko Togashi, Mobara (JP); Tsuneji Suzuki, Mobara (JP)

(73) Assignee: Mitsui Chemicals, Inc., Tokyo (JP)

( * ) Notice: Subject to any disclaimer, the term of this patent is extended or adjusted under 35 U.S.C. 154(b) by 327 days.

(21) Appl. No.: 10/433,004

(22) PCT Filed: Nov. 29, 2001

(86) PCT No.: PCT/JP01/10437

§ 371 (c)(1),
(2), (4) Date: May 29, 2003

(87) PCT Pub. No.: WO02/44194

PCT Pub. Date: Jun. 6, 2002

(65) Prior Publication Data

US 2004/0063926 A1   Apr. 1, 2004

(30) Foreign Application Priority Data

Nov. 29, 2000   (JP)   ............................ 2000-362081
Dec. 14, 2000   (JP)   ............................ 2000-380585

(51) Int. Cl.
*C07H 19/06*   (2006.01)
*C07H 19/09*   (2006.01)
(52) U.S. Cl. ................ 536/28.54; 536/28.53; 536/28.1; 536/27.1
(58) Field of Classification Search ............ 536/28.54, 536/28.53, 28.1, 27.1
See application file for complete search history.

(56) References Cited

FOREIGN PATENT DOCUMENTS

| JP | 02-059598 A | 2/1990 |
|---|---|---|
| JP | 06-092988 A | 4/1994 |
| WO | WO 96/13512 A2 | 5/1996 |
| WO | WO 00/09531 A2 | 2/2000 |

OTHER PUBLICATIONS

Greenberg et al., Journal of the American Chemical Society, vol. 119 (8), pp. 1828-1839, (1997).*

Codington et al., Carbohydrate Research, vol. 1 (6), 1966.*

Du et al., "A Practical Synthesis of l-FMAU From l-Arabinose," *Nucleosides & Nucleotides*, 1999, pp. 187-195, 18(2), Marcel Dekker, Inc.

Zhang et al., "Improved Synthesis of 2-Deoxy-l-Ribose," *Nucleosides & Nucleotides*, 1999, pp. 2357-2365, 18(11&12), Marcel Dekker, Inc.

Pragnacharyulu et al., "Diastereomeric 5,6-Dihydrothymidines. Preparation, Stereochemical Assignments, and $MnO_2$ Oxidation Studies to Thymidines," *J. Org. Chem.*, 1995, pp. 3096-3099, 60, American Chemical Society.

Holy, A. et al., "Nucleic Acid Components and Their Analogues. CLIII. Preparation of 2'-Deoxy-L-Ribonucleosides of the Pyrimidine Series", Collection Czechoslov. Chem. Commun., (1972), vol. 27, pp. 4072-4087.

Sawai, Hiroaki et al., "Facile Synthesis of 5-Substituted Arabinofuranosyluracil Derivatives", Chemistry Letters, (1994), pp. 605-606.

Camara, F. et al., "Synthesis of L-Analogues of 1-(2',3'-Dideoxy-β-D-glycero-pent-2-enofuranosyl)thymine", Pharm. Pharmacol. Commun., (1999), vol. 5, pp. 225-231.

Skarvic, Vinko et al., "Synthesis of β-D-Arabinofurano [1',2':4,5]oxa(thia)zolidines", J. Chem. Soc. Perkin Trans. I., (1985), pp. 779-783.

Greenberg, Marc M. et al., "DNA Damage Induced via 5,6-Dihydro-thymid-5-yl in Single-Stranded Oligonucleotides", J. Am. Chem. Soc., (1997), vol. 119, No. 8, pp. 1828-1839.

Jung, Michael E. et al., "A *de Novo* Synthesis of Ethyl 2-Deoxy-L-Ribosides", Tetrahedron Letters, (1998), vol. 39, pp. 4615-4618.

Chemical Abstracts, (1966), vol. 64, Abstract No. 15963(b).

* cited by examiner

*Primary Examiner*—James O. Wilson
*Assistant Examiner*—Howard V. Owens, Jr.
(74) *Attorney, Agent, or Firm*—Buchanan Ingersoll PC

(57) ABSTRACT

A novel method has been found to produce 2,2'-anhydro-1-(β-L-arabinofuranosyl)thymine as a novel useful intermediate compound. A novel method has been further found to produce thymidine from 2,2'-anhydro-1-(β-L-arabinofuranosyl)thymine. A novel method has been further found to L-2'-deoxyribose derivatives as a useful synthetic intermediate through L-2,2'-anhydro-5,6-dihydrocyclouridine derivative. According to these methods, synthesis of various L-nucleic acid derivatives, synthesis of which has been difficult till now.

17 Claims, No Drawings

US 7,125,983 B2

L-NUCLEIC ACID DERIVATIVES AND PROCESS FOR THE SYNTHESIS THEREOF

TECHNICAL FIELD

The present invention relates to novel processes for synthesis of L-nucleic acid derivatives useful as a medicine, as well as to synthesis intermediates therefor.

BACKGROUND ART

Nucleic acids occurring in nature are constituent components of DNA or RNA and the skeletons thereof have been used in a variety of medicines. Nucleic acids occurring in nature have a D-steric configuration and, therefore, D-nucleic acid derivatives have been used in medicines. In recent years, however, the meritorious effect of L-nucleic acid derivatives which are unnatural products, have been found and active development is under way for such L-nucleic acid derivatives. For example, clinical tests are under way using L-FMAU [1-(2'-deoxy-2'-fluoro-β-L-arabinofuranosyl)thymine], LdT [1-(β-L-arabinofuranosyl)thymine], a L-dc derivative [1-(2'-deoxy-β-L-arabinofuranosyl)cytidine derivative] or the like, and also studies are under way for processes for synthesis of such L-nucleic acid derivatives. In producing a L-nucleic acid derivative, it is necessary to use a L-saccharose as a basic skeleton and raw material for the derivative; however, this L-saccharose or a derivative thereof does not substantially occur in nature. L-arabinose is one of limited kinds of L-saccharoses occurring in nature and is available industrially. Hence, L-arabinose has generally been used as a raw material in synthesis of L-nucleic acid derivative.

In the case of, for example, L-FMAU, it is obtained by, as described in Nucleosides & Nucleotides, 18(2), 187–195 (1999), synthesizing, from L-arabinose, a corresponding L-saccharose moiety (3,5-di-O-benzoyl-1-bromo-2-deoxy-2-fluoro-β-L-arabinofuranose), reacting it with a silylated thymine, and conducting deprotection. However, there remain problems that the synthesis of L-saccharose moiety comprises 12 steps and the whole process consists of 14 steps in total and is long and that these steps comprise those difficult to conduct industrially, such as chromic acid oxidation and the like. Also in the synthesis of LdT or L-dc derivative, they are obtained by reacting a L-saccharose moiety [1-chloro-3,5-di-O-(p-chlorobenzoyl)-2-deoxy-L-ribofuranose] with a silylated thymine. This L-saccharose moiety is synthesized from L-arabinose, as described in Nucleosides & Nucleotides, 18(11), 2356 (1999); however, this synthesis comprises 9 steps and the whole process consists of 11 steps in total and is long, there are used sodium hydride, carbon disulfide, methyl iodide, diphenylsilane, etc. in the deoxy step, and thus there remain problems of safety and cost in industrial production.

Meanwhile, it is considered to apply a process which has been established by the past studies on synthesis of D-nucleic acid derivative. For example, a 2,2'-anhydro-1-(β-D-arabinofuranosyl)thymine derivative is known as an important synthesis intermediate which can be developed into a variety of D-thymidine derivatives. Of synthesis processes therefor, one having industrial applicability is a process which comprises reacting a D-ribose derivative with a thymine derivative to obtain 2'-hydroxythymidine and then subjecting it to cyclization to obtain a 2,2'-anhydro-1-(β-D-arabinofuranosyl)thymine derivative. However, in applying this process to synthesis of L-nucleic acid, L-ribose (necessary as a raw material) does not substantially occur in nature and is difficult to obtain; therefore, the above process is unapplicable to the synthesis of a 2,2'-anhydro-1-(β-L-arabinofuranosyl)thymine derivative. The following processes are also known as a synthesis process using D-arabinose as a raw material.

(1) A process which comprises subjecting, to ring closure using potassium t-butoxide, an arabinoaminooxazoline-α-bromomethylacrylic acid ester addition product obtained from arabinoaminooxazoline and an α-bromomethylacrylic acid ester to obtain 2,2'-anhydro-1-(β-D-arabinofuranosyl)thymine (JP-A-6-92988).

(2) A process which comprises reacting arabinoaminooxazoline with methyl β-bromomethacrylate in the presence of triethylamine-diethylaminopyridine to synthesize a 2,2'-anhydro-1-(β-D-arabinofuranosyl)thymine derivative (JP-A-2-59598).

(3) A process which comprises protecting the hydroxyl group of arabinoaminooxazoline with an organosilicon compound such as t-butyldimethylsilyl group or the like, then reacting the resulting compound with methyl methacrylate, and subjecting the resulting adduct to dehydrogenation using manganese dioxide or dichlorodicyanoquinone to synthesize a 2,2'-anhydro-1-(β-D-arabinofuranosyl)thymine derivative [J. Org. Chem., 60(10), 3097 (1995)].

In the process (1), however, there is formed, in a fairly large amount, a hydrolysis product of the ester moiety of D-arabinoaminooxazoline-α-bromomethylacrylic acid ester addition product, resulting in a low yield; in the process (2), the reaction time is very long and the yield is low; in the process (3), the protection of hydroxyl and a special dehydrogenating agent are necessary. Thus, any process was not at a level of industrial applicability. Therefore, in order to industrially produce a L-nucleic acid derivative for use in medicine, a novel efficient synthesis process has been required.

DISCLOSURE OF THE INVENTION

The present invention aims at providing processes capable of producing a L-nucleic acid derivative in short steps and industrially, using, as a raw material, L-arabinose which is one of limited kinds of L-saccharoses available industrially. The present invention also aims at providing synthesis intermediates useful for production of a variety of L-nucleic acid derivatives.

The present inventors made an intensive study in order to develop a process for producing a L-nucleic acid derivative using L-arabinose as a raw material. As a result, the present inventors found a novel process for producing 2,2'-anhydro-1-(β-L-arabinofuranosyl)thymine represented by formula (5) which is a useful synthesis intermediate utilizable in synthesis of a variety of L-nucleic acid derivatives, by reacting L-arabinoaminooxazoline (easily obtainable from L-arabinose) with an acrylic acid derivative. The present inventors also found a novel process for producing a L-thymidine derivative by subjecting 2,2'-anhydro-1-(β-L-arabinofuranosyl)thymine to halogenation and dehalogenation. The present inventors also found a novel process for producing a L-2'-deoxyribose derivative which is a useful synthesis intermediate usable for synthesis of a variety of L-nucleic acid derivatives, via a L-2,2'-anhydro-5,6-dihydrocyclouridine derivative.

The present invention comprises the following modes.

[1] A process for producing L-thymidine, characterized by comprising:

(a) a step of reacting L-arabinoaminooxazoline represented by the following formula (1)

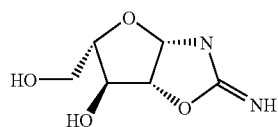
(1)

with an acrylic acid derivative represented by the following formula (2)

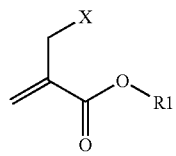
(2)

(wherein R1 is a lower alkyl group, and X is chlorine, a p-toluenesulfonyloxy group or a methanesulfonyloxy group) to synthesize a L-arabinoaminooxazoline derivative represented by the following formula (3)

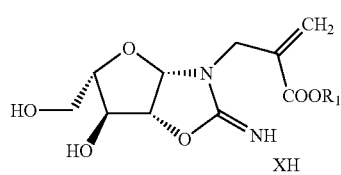
(3)

(wherein X and R1 have the same definitions as given above), (b) a step of reacting a base with the L-arabinoaminooxazoline derivative represented by the formula (3) to synthesize a L-2,2'-anhydronucleic acid derivative represented by the following formula (4)

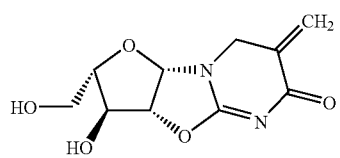
(4)

(c) a step of isomerizing the L-2,2'-anhydronucleic acid derivative represented by the formula (4) to synthesize 2,2'-anhydro-1-(β-L-arabinofuranosyl)thymine represented by the following formula (5)

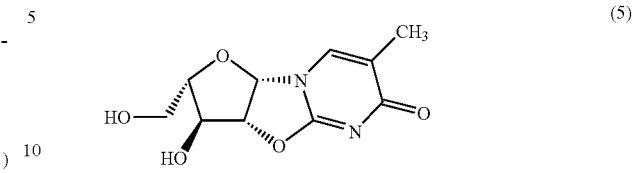
(5)

(d) a step of subjecting the 2,2'-anhydro-1-(β-L-arabinofuranosyl)thymine represented by the formula (5) to halogenation and subsequent protection, or protection and subsequent halogenation, or protection and simultaneous halogenation to synthesize a 2' position-halogenated L-thymidine derivative represented by the following formula (6)

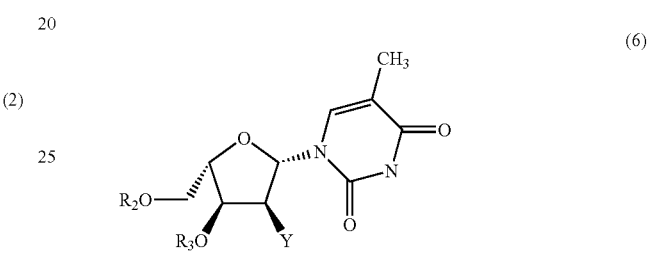
(6)

(wherein R2 and R3 are each independently a protecting group for hydroxyl group, and Y is a halogen atom), (e) a step of dehalogenation of the compound represented by the formula (6) to synthesize a L-thymidine derivative represented by the following formula (7)

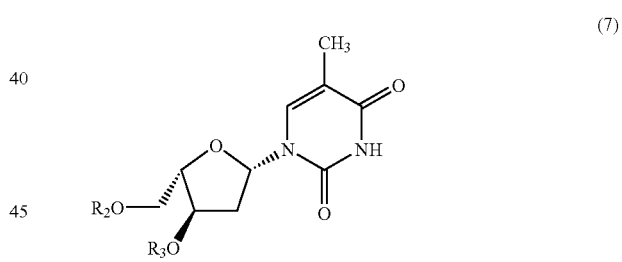
(7)

(wherein R2 and R3 have the same definitions as given above), and (f) a step of deblocking the compound represented by the formula (7) to synthesize L-thymidine.

[2] A process for producing 2,2'-anhydro-1-(β-L-arabinofuranosyl)thymine, characterized by comprising:

(a) a step of reacting L-arabinoaminooxazoline represented by the following formula (1)

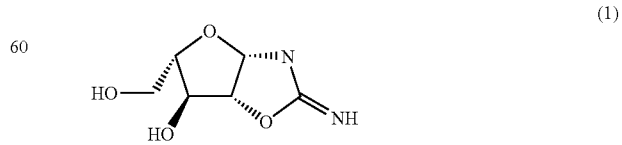
(1)

with an acrylic acid derivative represented by the following formula (2)

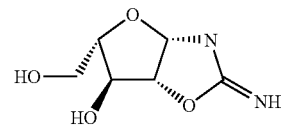 (1)

with an acrylic acid derivative represented by the following formula (2)

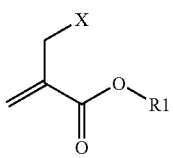 (2)

(wherein R1 is a lower alkyl group and X is chlorine, a p-toluenesulfonyloxy group or a methanesulfonyloxy group) to synthesize a L-arabinoaminooxazoline derivative represented by the following formula (3)

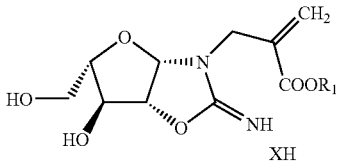 (3)

(wherein X and R1 have the same definitions as given above).

[4] A L-arabinoaminooxazoline derivative represented by the following formula (3)

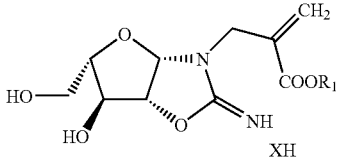 (3)

(wherein R1 is a lower alkyl group, and X is chlorine, a p-toluenesulfonyloxy group or a methanesulfonyloxy group).

[5] A process for producing a L-2,2'-anhydronucleic acid derivative, characterized by allowing a base to act on a

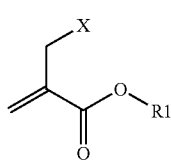 (2)

(wherein R1 is a lower alkyl group and X is chlorine, a p-toluenesulfonyloxy group or a methanesulfonyloxy group) to synthesize a L-arabinoaminooxazoline derivative represented by the following formula (3)

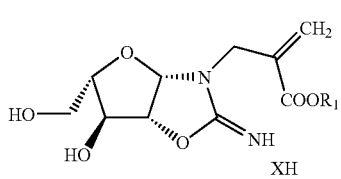 (3)

(wherein X and R1 have the same definitions as given above), (b) a step of allowing a base to act on the L-arabinoaminooxazoline derivative represented by the formula (3) to synthesize a L-2,2'-anhydronucleic acid derivative represented by the following formula (4)

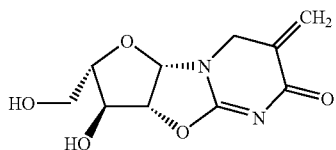 (4)

and (c) a step of isomerizing the a L-2,2'-anhydronucleic acid derivative represented by the formula (4) to synthesize 2,2'-anhydro-1-(β-L-arabinofuranosyl)thymine represented by the following formula (5)

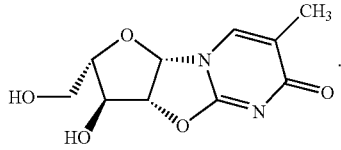 (5)

[3] A process for producing a L-arabinoaminooxazoline derivative, characterized by comprising:

a step of reacting L-arabinoaminooxazoline represented by the following formula (1)

L-arabinoaminooxazoline derivative represented by the following formula (3)

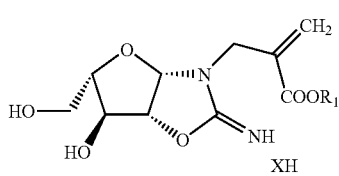
(3)

(wherein R1 is a lower alkyl group, and X is chlorine, a p-toluenesulfonyloxy group or a methanesulfonyloxy group) to synthesize a L-2,2'-anhydronucleic acid derivative represented by the following formula (4)

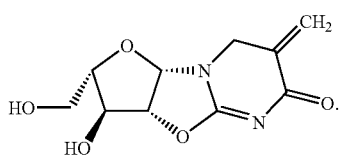
(4)

[6] A L-2,2'-anhydronucleic acid derivative represented by the following formula (4)

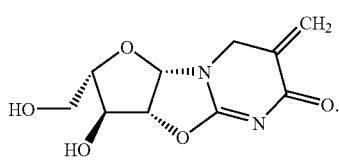
(4)

[7] A process for producing 2,2'-anhydro-1-(β-L-arabinofuranosyl)thymine, characterized by isomerizing a L-2,2'-anhydronucleic acid derivative represented by the following formula (4)

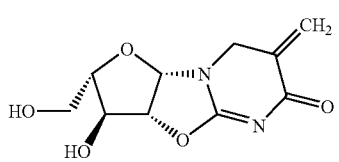
(4)

to synthesize 2,2'-anhydro-1-(β-L-arabinofuranosyl)thymine represented by the following formula (5)

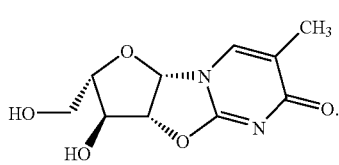
(5)

[8] 2,2'-Anhydro-1-(β-L-arabinofuranosyl)thymine represented by the following formula (5)

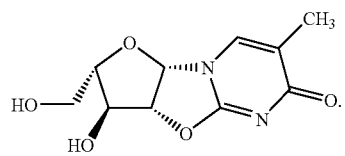
(5)

[9] A process for producing a 2' position-halogenated L-thymidine derivative, characterized by subjecting 2,2'-anhydro-1-(β-L-arabinofuranosyl)thymine represented by the following formula (5)

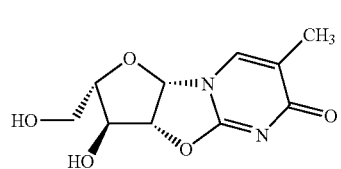
(5)

to halogenation and subsequent protection, or protection and subsequent halogenation, or protection and simultaneous halogenation to synthesize a 2' position-halogenated L-thymidine derivative represented by the following formula (6)

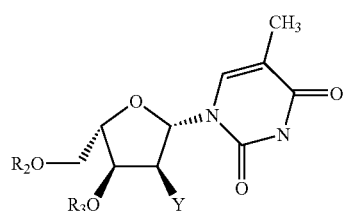
(6)

(wherein R2 and R3 are each independently a protecting group for hydroxyl group, and Y is a halogen atom).

[10] A 2' position-halogenated L-thymidine derivative represented by the following formula (6)

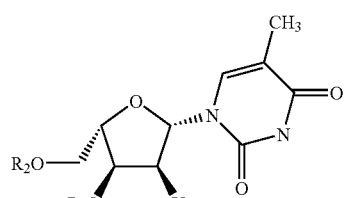
(6)

(wherein R2 and R3 are each independently a protecting group for hydroxyl group, and Y is a halogen atom).

[11] A process for producing a L-thymidine derivative, characterized by subjecting a compound represented by the following formula (6)

(6)

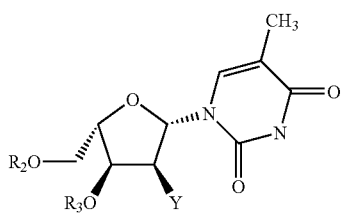

(wherein R2 and R3 are each independently a protecting group for hydroxyl group, and Y is a halogen atom) to dehalogenation to synthesize a L-thymidine derivative represented by the following formula (7)

(7)

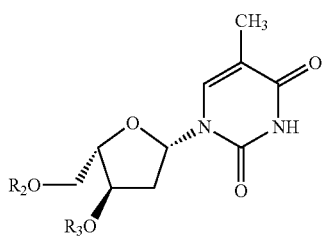

(wherein R2 and R3 have the same definitions as given above).

[12] A L-thymidine derivative represented by the following formula (7)

(7)

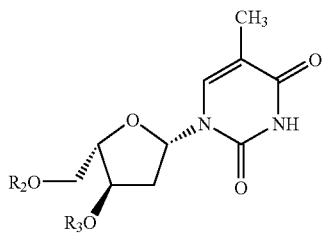

(wherein R2 and R3 are each independently a protecting group for hydroxyl group).

[13] A process for producing a L-2-deoxyribose derivative, characterized by comprising:

I. a step of reacting L-arabinoaminooxazoline represented by the following formula (1)

(1)

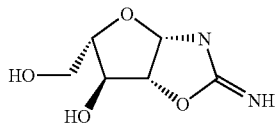

with a lower-alkyl acrylic acid ester to synthesize L-2,2'-anhydro-1-(β-arabinofuranosyl)-5,6-dihydrouridine represented by the following formula (8)

(8)

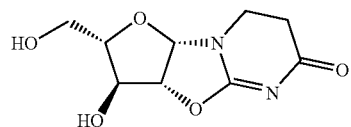

II. a step of protection of the L-2,2'-anhydro-1-(β-arabinofuranosyl)-5,6-dihydrouridine represented by the formula (8) to synthesize a L-2,2'-anhydro-5,6-dihydrouridine derivative represented by the following formula (9)

(9)

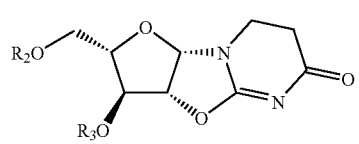

(wherein R2 and R3 are each independently a protecting group for hydroxyl group), III. a step of halogenation of the L-2,2'-anhydro-5,6-dihydrouridine derivative represented by the formula (9) to synthesize a 2' position-halogenated L-5,6-dihydrouridine derivative represented by the following formula (10)

(10)

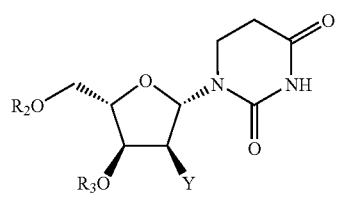

(wherein R2, R3 and Y have the same definitions as given above),

IV. a step of subjecting the compound represented by the formula (10) to dehalogenation, or dehalogenation and subsequent deblocking, or deblocking and subsequent dehalogenation, or deblocking and simultaneous dehalogenation to synthesize a L-2'-deoxy-5,6-dihydoruridine derivative represented by the following formula (11)

(11)

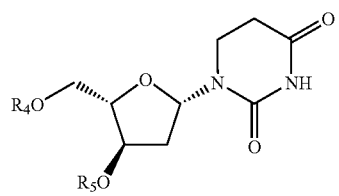

(wherein R4 and R5 are each independently a hydrogen atom or a protecting group for hydroxyl group), and V. a step of a decomposition reaction of the compound represented by the formula (11) to obtain a L-2-deoxyribose derivative represented by the following formula (12)

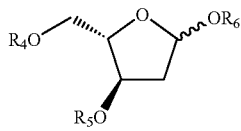
(12)

(wherein R4 and R5 have the same definitions as given above, and R6 is hydrogen, a methyl group or an ethyl group).

[14] A process for producing a L-2,2'-anhydro-5,6-dihydrouridine derivative, characterized by comprising:

I. a step of reacting L-arabinoaminooxazoline represented by the following formula (1)

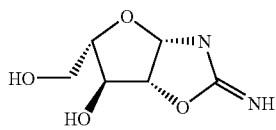
(1)

with a lower-alkyl acrylic acid ester to synthesize L-2,2'-anhydro-1-(β-arabinofuranosyl)-5,6-dihydrouridine represented by the following formula (8)

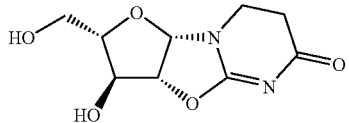
(8)

and

II. a step of subjecting the compound represented by the formula (8) to protection to synthesize a L-2,2'-anhydro-5,6-dihydrouridine derivative represented by the following formula (9)

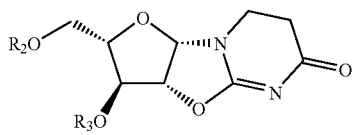
(9)

(wherein R2 and R3 are each independently a protecting group for hydroxyl group).

[15] A L-2,2'-anhydro-5,6-dihydrouridine derivative represented by the formula (9)

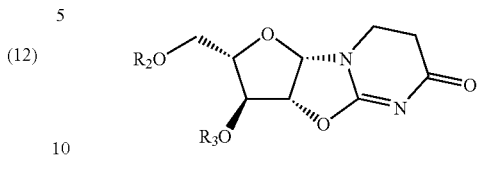
(9)

(wherein R2 and R3 are each independently a protecting group for hydroxyl group).

[16] A process for producing a 2' position-halogenated L-5,6-dihydrouridine derivative, characterized by halogenating a compound represented by the following formula (9)

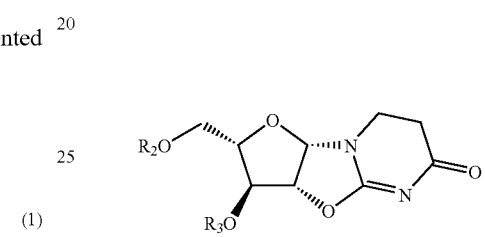
(9)

(wherein R2 and R3 are each independently a protecting group for hydroxyl group) to synthesize a 2' position-halogenated L-5,6-dihydrouridine derivative represented by the following formula (10)

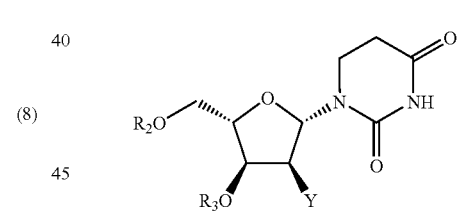
(10)

(wherein R2, R3 have the same definition as given above and Y is a halogen atom).

[17] A 2' position-halogenated L-5,6-dihydrouridine derivative represented by the following formula (10)

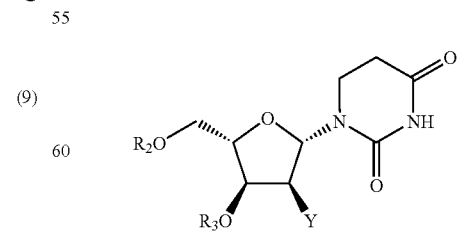
(10)

(wherein R2 and R3 are each independently a protecting group for hydroxyl group, and Y is a halogen atom).

[18] A process for producing a L-2'-deoxy-5,6-dihydrouridine derivative, characterized by subjecting a compound represented by the following formula (10)

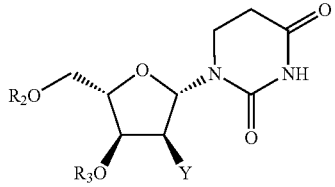
(10)

(wherein R2 and R3 are each independently a protecting group for hydroxyl group, and Y is a halogen atom) to dehalogenation, or dehalogenation and subsequent deblocking, or deblocking and subsequent dehalogenation, or deblocking and simultaneous dehalogenation to synthesize a L-2'-deoxy-5,6-dihydrouridine derivative represented by the following formula (11)

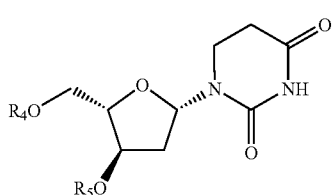
(11)

(wherein R4 and R5 are each independently a hydrogen atom or a protecting group for hydroxyl group).

[19] A L-2'-deoxy-5,6-dihydrouridine derivative represented by the following formula (11)

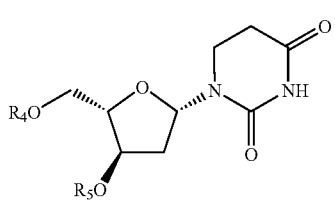
(11)

(wherein R4 and R5 are each independently a hydrogen atom or a protecting group for hydroxyl group).

[20] A process for producing a L-2-deoxyribose derivative, characterized by decomposing a L-2'-deoxy-5,6-dihydrouridine derivative represented by the following formula (11)

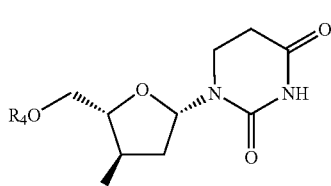
(11)

(wherein R4 and R5 are each independently a hydrogen atom or a protecting group for hydroxyl group) to obtain a L-2-deoxyribose derivative represented by the following formula (12)

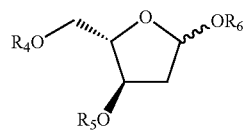
(12)

(wherein R4 and R5 have the same definitions as given above, and R6 is hydrogen, a methyl group or an ethyl group).

BEST MODE FOR CARRYING OUT THE INVENTION

The present invention is described in more detail below.

The term "lower" in lower alkyl group, lower alkoxy group or the like can be exemplified by 1 to 4 carbon atoms. As the lower alkyl group, there can be mentioned, for example, alkyl groups of 1 to 4 carbon atoms, such as methyl group, ethyl group, propyl group, isopropyl group, n-butyl group, isobutyl group, sec-butyl group, tert-butyl group and the like.

The base used in the step (b), etc. is alkali metal alkoxide, alkali metal carbonate, alkali metal bicarbonate, alkali metal hydroxide, alkali metal hydride, alkali metal, organic base, basic ion exchange resin, or the like, and has a function capable of giving rise to a ring closure reaction from a formula (3) compound to a formula (4) compound in the step (b). A compound selected from the above can be used in the step (b).

The protecting group for hydroxyl group refers to a protecting group which can be removed by a chemical method such as hydrogenolysis, hydrolysis, photo-decomposition or the like. Such a group includes formyl group, acyl group, silyl group, alkyl group, aralkyl group and carbonyl group. Of these, preferred are formyl group, aliphatic acyl group, aromatic acyl group, silyl group, alkoxyalkyl group, halogenated alkyl group, aralkyl group, alkoxycarbonyl group and aralkyloxycarbonyl group.

As the aliphatic acyl group, there can be mentioned alkylcarbonyl group or halogen-substituted lower alkylcarbonyl group.

As specific examples of the alkylcarbonyl group, there can be mentioned acetyl group, propionyl group, butyryl group, isobutyryl group, pentanoyl group, pivaloyl group, valeryl group, isovaleryl group, octanoyl group, nonylcarbonyl group, decylcarbonyl group, 3-methylnonylcarbonyl group, 8-methylnonylcarbonyl group, 3-ethyloctylcarbonyl group, 3,7-dimethyloctylcarbonyl group, undecylcarbonyl group, dodecylcarbonyl group, tridecylcarbonyl group, tetradecylcarbonyl group, pentadecylcarbonyl group, hexadecylcarbonyl group, 1-methylpentadecylcarbonyl group, 14-methylpentadecylcarbonyl group, 13,13-dimethyltetradecylcarbonyl group, heptadecylcarbonyl group, 15-methylhexadecylcarbonyl group and octadecylcarbonyl group.

As specific examples of the halogen-substituted lower alkylcarbonyl group, there can be mentioned chloroacetyl group, dichloroacetyl group, trichloroacetyl group and trifluoroacetyl group.

As the aromatic acyl group, there can be mentioned arylcarbonyl group, halogen-substituted arylcarbonyl group, lower-alkylated arylcarbonyl group, lower alkoxy arylcarbonyl group, nitrated arylcarbonyl group, lower alkoxy carbonylated arylcarbonyl group and arylated arylcarbonyl group.

As specific examples of the arylcarbonyl group, there can be mentioned benzoyl group, α-naphthoyl group and β-naphthoyl group.

As specific examples of the halogen-substituted arylcarbonyl group, there can be mentioned 2-fluorobenzoyl group, 3-fluorobenzoyl group, 4-fluorobenzoyl group, 2-chlorobenzoyl group, 3-chlorobenzoyl group, 4-chlorobenzoyl group, 2-bromobenzoyl group, 3-bromobenzoyl group, 4-bromobenzoyl group, 2,4-dichlorobenzoyl group, 2,6-dichlorobenzoyl group, 3,4-dichlorobenzolyl group and 3,5-dichlorobenzoyl group.

As specific examples of the lower-alkylated arylcarbonyl group, there can be mentioned 2-toluoyl group, 3-toluoyl group, 4-toluoyl group and 2,4,6-trimethylbenzoyl group.

As specific examples of the lower-alkoxy arylcarbonyl group, there can be mentioned 2-anisolyl group, 3-anisoyl group and 4-anisoyl group.

As specific examples of the nitrated arylcarbonyl group, there can be mentioned 2-nitrobenzoyl group, 3-nitrobenzoyl group, 4-nitrobenzoyl group and 3,5-dinitrobenzoyl group.

As specific examples of the lower-alkoxy carbonylated arylcarbonyl group, 2-(methoxycarbonyl)benzoyl group, etc. can be shown. As specific examples of the arylated arylcarbonyl group, 4-phenylbenzoyl group, etc. can be shown.

As the silyl group, there can be mentioned lower alkylsilyl group and aryl-substituted lower alkylsilyl group.

As specific examples of the lower alkylsilyl group, there can be shown trimethylsilyl group, triethylsilyl group, isopropyldimethylsilyl group, methyldiisopropylsilyl group and triisopropylsilyl group.

As specific examples of the aryl-substituted lower alkylsilyl group, there can be shown diphenylmethylsilyl group, diphenylisopropylsilyl group, tert-butyldiphenylsilyl group and phenyldiisopropylsilyl group.

As the aralkyl group, there can be mentioned aralkyl groups, for example, aryl-substituted lower alkyl groups such as benzyl group, α-naphthylmethyl group, β-naphthylmethyl group, diphenylmethyl group, triphenylmethyl group and the like. The aralkyl group may be substituted and, as the substituted aralkyl group, there can be mentioned, for example, lower alkyl-substituted aralkyl group, lower alkoxy-substituted aralkyl group, nitro-substituted aralkyl group, halogen-substituted aralkyl group and cyano-substituted aralkyl group.

As specific examples of these groups, there can be mentioned 2-methylbenzyl group, 3-methylbenzyl group, 4-methylbenzyl group, 2,4,6-trimethylbenzyl group, 2-methoxybenzyl group, 3-methoxybenzyl group, 4-methoxybenzyl group, 2-nitrobenzyl group, 3-nitrobenzyl group, 4-nitrobenzyl group, 2-chlorobenzyl group, 3-chlorobenzyl group, 4-chlorobenzyl group, 2-bromobenzyl group, 3-bromobenzyl group, 4-bromobenzyl group, 2-cycanobenzyl group, 3-cyanobenzyl group and 4-cyanobenzyl group.

As the aralkyloxycarbonyl group, there can be mentioned lower alkyl-substituted aralkyloxycarbonyl group, lower alkoxy-substituted aralkyloxycarbonyl group, nitro-substituted aralkyloxycarbonyl group, halogen-substituted aralkyloxycarbonyl group and cyano-substituted aralkyloxycarbonyl group.

As specific examples thereof, there can be mentioned 2-methylbenzyloxycarbonyl group, 3-methylbenzyloxycarbonyl group, 4-methylbenzyloxycarbonyl group, 2,4,6-trimethylbenzyloxycarbonyl group, 2-methoxybenzyloxycarbonyl group, 3-methoxybenzyloxycarbonyl group, 4-methoxybenzyloxycarbonyl group, 2-nitrobenzyloxycarbonyl group, 3-nitrobenzyloxycarbonyl group, 4-nitrobenzyloxycarbonyl group, 2-chlorobenzyloxycarbonyl group, 3-chlorobenzyloxycarbonyl group, 4-chlorobenzyloxycarbonyl group, 2-bromobenzyloxycarbonyl group, 3-bromobenzyloxycarbonyl group, 4-bromobenzyloxycarbonyl group, 2-cyanobenzyloxycarbonyl group, 3-cyanobenzyloxycarbonyl group and 4-cyanobenzyloxycarbonyl group.

As the alkoxycarbonyl group, there can be mentioned lower alkoxycarbonyl group, halogen-substituted alkoxycarbonyl compound and alkylsilyl-substituted alkoxycarbonyl group.

As specific examples of the lower alkoxycarbonyl group, there can be shown methoxycarbonyl group, ethoxycarbonyl group, propoxycarbonyl group, butoxycarbonyl group, sec-butoxycarbonyl group and tert-butoxycarbonyl group.

As specific examples of the halogen-substituted alkoxycarbonyl group, there can be shown 2,2,2-trichloroethoxycarbonyl group, etc. As specific examples of the lower alkylsilyl-substituted alkoxycarbonyl group, there can be shown 2-trimethylsilylethoxycarbonyl group, etc.

As the alkyl group, the previously mentioned lower alkyl groups can be mentioned. The alkyl group may be substituted. As the substituted alkyl group, there can be mentioned, for example, alkoxyalkyl groups such as alkoxy-substituted lower alkyl group (e.g. methoxymethyl group, ethoxymethyl group, 2-methoxyethyl group, 2-methoxyethoxymethyl group, which have a lower alkyl group); and halogenated alkyl groups such as halogen-substituted lower alkyl group (e.g. 2,2,2-trichloroethyl group).

Of these, preferred are aliphatic acyl group, aromatic acyl group and aralkyl group; more preferred are acetyl group, benzoyl group, 4-toluoyl group, 4-chlorobenzoyl group, trityl group, dimethoxytrityl group and benzyl group.

As the halogen, there can be mentioned chlorine, bromine, iodine, fluorine, etc.

The individual reactions are each described below. Isolation of intended product from reaction mixture can be conducted by an ordinary separation means such as extraction, concentration, crystallization, neutralization, filtration, recrystallization, column chromatography or the like. As the reaction solvent, there can be used, unless particularly specified, one kind or an admixture of two or more kinds, selected from protic solvents such as water, methanol, ethanol, propanol and the like, and aprotic solvents such as benzene, toluene, xylene, 1,2-dichloroethane, dimethylformamide, dimethyl sulfoxide, dimethyl acetamide, dimethyl imidazolidinone, N-methylpyrrolidone, ethyl acetate, dioxane, tetrahydrofuran and the like. There is no particular restriction as to the reaction temperature, and a temperature ranging from −20° C. to the reflux temperature of the solvent used can be selected.

In the present invention, first, the L-β-arabinoaminooxazoline represented by the formula (1) can be easily synthesized by using a known synthesis process [J. Org. Chem., 41(10), 1828, (1976)] of D-β-arabinoaminooxazoline and reacting easily available L-arabinose with cyanamide in the presence of a base.

The acrylic acid derivative represented by the formula (2) is generally available as a raw material but can be easily synthesized by subjecting an α-hydroxymethylacrylic acid ester to chlorination, p-toluenesulfonylation, or methanesulfonylation. As the R1 constituting the ester, a lower alkyl group can be used. As the lower alkyl group, there can be used methyl group, ethyl group, propyl group, isopropyl group, n-butyl group, isobutyl group, sec-butyl group, tert-butyl group, etc.

The L-arabinoaminooxazoline derivative represented by the formula (3) can be obtained by reacting L-β-arabinoaminooxazoline represented by the formula (1) with an acrylic acid derivative represented by the formula (2) in a solvent. In the reaction, a polymerization inhibitor such as hydroquinone or the like can be added.

The L-2,2'-anhydronucleic acid derivative represented by the formula (4) can be obtained by subjecting a L-arabinoaminooxazoline derivative represented by the formula (3) to ring closure in a solvent in the presence of a base. As specific examples of the base, there can be used inorganic bases such as sodium hydroxide, potassium hydroxide, calcium hydroxide, barium hydroxide, sodium carbonate, potassium carbonate, sodium hydrogencarbonate, potassium hydrogencarbonate, sodium acetate and the like; alkali metal alkoxides such as sodium methoxide, sodium ethoxide, potassium tert-butoxide and the like; organic bases such as pyridine, triethylamine, dimethylaniline, DBU and the like; and basic resins such as Amberlite IR A400 and the like. In the reaction, a polymerization inhibitor such as hydroquinone or the like can be added.

The 2,2'-anhydro-1-(β-L-arabinofuranosyl)thymine represented by the formula (5) can be obtained by isomerizing a L-2,2'-anhydronucleic acid derivative represented by the formula (4) in a solvent using a metal catalyst, an acid, a base, a light or the like. The compound can also be synthesized directly from a L-arabinoaminooxazoline derivative represented by the formula (3), without taking out the L-2,2'-anhydronucleic acid derivative represented by the formula (4). As to the metal catalyst, there is no particular restriction as long as it can promote the isomerization; however, a transition metal catalyst is preferred. As the transition metal, there can be mentioned Pd, Rh, Ru, Pt, etc. These transition metals can also be used in an oxidized form such as oxide, chloride or the like, or in a ligand-attached form. These metal catalysts can be used per se or by being loaded on active carbon, alumina, silica or the like. The reaction can also be conducted in a hydrogen atmosphere, or in an inert gas atmosphere, or in an air atmosphere. In the reaction, a polymerization inhibitor such as hydroquinone or the like can be added. As the acid, there can be mentioned inorganic acids such as hydrochloric acid, sulfonic acid, phosphoric acid and the like; organic acids such as formic acid, acetic acid, methanesulfonic acid, p-toluenesulfonic acid and the like; acidic resins such as Amberlite 15 and the like; and so forth. As the base, there can be used inorganic bases such as sodium hydroxide, potassium hydroxide, calcium hydroxide, barium hydroxide, sodium carbonate, potassium carbonate, sodium hydrogencarbonate, potassium hydrogencarbonate, sodium acetate and the like; alkali metal alkoxides such as sodium methoxide, sodium ethoxide, potassium tert-butoxide and the like; organic bases such as pyridine, triethylamine, dimethylaniline, DBU and the like; basic resins such as Amberlite IR A400 and the like; and so forth.

The 2' position-halogenated L-thymidine derivative represented by the formula (6) can be obtained by any of a process of subjecting 2,2'-anhydro-1-(β-L-arabinofuranosyl)thymine to halogenation and subsequent protection in a solvent, a process of subjecting the thymine to protection and subsequent halogenation, and a process of subjecting the thymine to protection and simultaneous halogenation. As the halogenating agent, there can be mentioned halides such as hydrobromic acid, hydrochloric acid, pyridine hydrobromide, pyridine hydrochloride, alkyl ammonium halide, sodium bromide and the like. As the protecting group, there can be used the above-mentioned ordinary protecting groups which can be removed by a chemical method such as hydrogenolysis, hydrolysis, photo decomposition or the like. Preferred are formyl group, acyl group, silyl group, alkyl group, aralkyl group and carbonyl group. Particularly preferred are formyl group, aliphatic acyl group, aromatic acyl group, silyl group, alkoxyalkyl group, halogenated alkyl group, aralkyl group, alkoxycarbonyl group and aralkyloxycarbonyl group. When protection and halogenation are conducted simultaneously, the halogenation can be conducted by using a halide R—X corresponding to the protecting group R. As the R—X, there can be mentioned aliphatic acyl chloride, aliphatic acyl bromide, aromatic acyl chloride, aromatic acyl bromide, aralkyl chloride, aralkyl bromide, etc. Thus, acetylation and halogenation can be conducted simultaneously by using acetyl chloride, acetyl bromide, or the like; benzoylation and halogenation can be conducted simultaneously by using benzoyl chloride, benzoyl bromide or the like. There is no particular restriction as to the equivalents of the halogenating reagent, but they are preferably 1.1 to 10 equivalents relative to the 2,2'-anhydro-1-(β-L-arabinofuranosyl)thymine represented by the formula (5).

The L-thymidine derivative represented by the formula (7) can be obtained by subjecting a 2' position-halogenated L-thymidine derivative represented by the formula (6) to dehalogenation in a solvent. As the method for dehalogenation, there can be used a method of conducting hydrogenation using a transition metal catalyst, a method using a metal hydride, and a method of conducting reduction using an organotin compound (e.g. tributyltin hydride) or an organosilicon compound (e.g. diphenylsilane) in the presence of a radical initiator such as AIBN. In the method of conducting hydrogenation using a transition metal catalyst, the hydrogen pressure employed may be ordinary pressure to 4.905 MPa, preferably 0.0981 to 2.943 MPa. The reaction may be conducted in the presence or absence of a base. As the transition metal catalyst, there are preferred Pd, Rh, Ru, Pt, etc. These transition metals may also be used in an oxidized form such as oxide, chloride or the like, or in a ligand-attached form. These metal catalysts can be used per se or by being loaded on active carbon, alumina, silica or the like. A palladium catalyst is preferred particularly. The catalyst is used in an amount of 1 to 100% (weight/weight), preferably 1 to 50% relative to the compound used. As to the base, there is no particular restriction as long as it does not impair the reaction and functions as an acid-removing agent; however, there are mentioned organic bases (e.g. pyridine, triethylamine and dimethylaniline), sodium hydroxide, sodium carbonate, sodium hydrogencarbonate, potassium carbonate, sodium acetate, etc.

The synthesis of L-thymidine from the L-2'-thymidine derivative represented by the formula (7) can be conducted by an ordinary method of subjecting the R2 and R3 (protecting groups) of the formula (7) to deblocking. That is, the R2 and R3 can be removed by a chemical method such as hydrogenolysis, hydrolysis, photo-decomposition or the like.

The L-2,2'-anhydro-1-(β-arabinofuranosyl)-5,6-dihydrouridine represented by the formula (8) can be obtained by applying a known process [J. Org. Chem., 37(21), 3290, (1972)] and reacting a L-arabinoaminooxazoline represented by the formula (1) with an acrylic acid ester.

The L-2,2'-anhydro-5,6-dihydrouridine derivative represented by the formula (9) can be obtained by protecting the hydroxyl group of L-2,2'-anhydro-1-(β-arabinofuranosyl)-5,6-dihydrouridine with an ordinary protecting group. As the protecting group, there can be used the above-mentioned ordinary protecting groups which can be removed by a chemical method such as hydrogenolysis, hydrolysis, photodecomposition or the like. As preferred protecting groups, there are formyl group, acyl group, silyl group, alkyl group, aralkyl group and carbonyl group. As particularly preferred protecting groups, there can be mentioned formyl group, aliphatic acyl group, aromatic acyl group, silyl group, alkoxyalkyl group, halogenated alkyl group, aralkyl group, alkoxycarbonyl group and aralkyloxycarbonyl group.

The 2' position-halogenated L-5,6-dihydrouridine derivative represented by the formula (10) can be obtained by halogenating a L-2,2'-anhydro-5,6-dihydrouridine derivative represented by the formula (9) in a solvent, or by subjecting L-2,2'-anhydro-1-(β-arabinofuranosyl)-5,6-dihydrouridine represented by the formula (8) to protection and halogenation simultaneously. As the halogenating agent used, there can be mentioned halides such as hydrobromic acid, hydrochloric acid, pyridine hydrobromide, pyridine hydrochloride, alkyl ammonium halide, sodium bromide and the like. As the protecting group, there can be used the above-mentioned ordinary protecting groups which can be removed by a chemical method such as hydrogenolysis, hydrolysis, photo decomposition or the like. When protection and halogenation are conducted simultaneously, it can be conducted by using a halide R-X corresponding to the protecting group R. As the R-X, there can be mentioned aliphatic acyl chloride, aliphatic acyl bromide, aromatic acyl chloride, aromatic acyl bromide, aralkyl chloride, aralkyl bromide, etc. Thus, acetylation and halogenation can be conducted simultaneously by using acetyl chloride, acetyl bromide or the like; benzoylation and halogenation can be conducted simultaneously by using benzoyl chloride, benzoyl bromide or the like. There is no particular restriction as to the equivalents of the halogenating reagent used, but they are preferably 1.1 to 10 equivalents relative to the 2,2'-anhydro-1-(β-L-arabinofuranosyl)-5,6-dihydrouridine derivative.

The 2'-deoxy-β-L-5,6-dihydrouridine derivative represented by the formula (11) can be obtained by subjecting a 2' position-halogenated L-5,6-dihydrouridine derivative represented by the formula (10) to dehalogenation in a solvent.

In this step, deblocking may be conducted as necessary.

As the method for dehalogenation, there can be used a method of conducting hydrogenation using a transition metal catalyst, a method using a metal hydride, and a method of conducting reduction using an organotin compound (e.g. tributyltin hydride) or an organosilicon compound (e.g. diphenylsilane) in the presence of a radical initiator such as AIBN. In the method of conducting hydrogenation using a transition metal catalyst, the hydrogen pressure employed can be ordinary pressure to 4.905 MPa, preferably 0.0981 to 2.943 MPa. The reaction may be conducted in the presence or absence of a base. As the transition metal catalyst, there are preferred Pd, Rh, Ru, Pt, etc. These transition metals may also be used in an oxidized form such as oxide, chloride or the like, or in a ligand-attached form. These metal catalysts can be used per se or by being loaded on active carbon, alumina, silica or the like. A palladium catalyst is preferred particularly. The catalyst is used in an amount of 1 to 100% (weight/weight), preferably 1 to 50% relative to the compound used. As to the reaction temperature, there is no particular restriction, and it may be 0° C. to the reflux temperature. As to the base, there is no particular restriction as long as it does not impair the reaction and functions as an acid-removing agent; however, there are mentioned organic bases (e.g. pyridine, triethylamine and dimethylaniline), sodium hydroxide, sodium carbonate, sodium hydrogencarbonate, potassium carbonate, sodium acetate, etc.

The L-2'-deoxyribose derivative represented by the formula (12) can be obtained by decomposing the 5,6-dihydrouridine ring of a L-2'-deoxy-β-5,6-dihydrouridine derivative represented by the formula (11). In the decomposition reaction, an acid is preferably used. As the acid, there can be mentioned inorganic acids such as hydrochloric acid, sulfuric acid, phosphoric acid and the like; organic acids such as formic acid, acetic acid, methanesulfonic acid, p-toluenesulfonic acid and the like; acidic resins such as Amberlite 15 and the like; and so forth. When a mixed solvent is used, the reaction may be conducted in the presence of a phase transfer catalyst. As the phase transfer catalyst, there can be mentioned, for example, quaternary ammonium salts such as triethylbenzylammonium chloride, triethylammonium bromide, tetramethylammonium chloride, tetramethylammonium bromide, tetraethylammonium chloride, tetraethylammonium bromide, tetrabutylammonium chloride, tetrabutylammonium bromide, tetrabutylammonium hydrogen sulfite and the like; and crown ethers such as 18-crown-6-ether, 12-crown-6-ether, dibenzo-24-crown-8-ether, dicyclohexano-24-crown-8-ether and the like.

EXAMPLES

The present invention is described in more detail below by way of Examples. However, the present invention is in no way restricted thereto.

Example 1

Production of L-arabinoaminooxazoline-α-chloromethylacrylic acid adduct

Thionyl chloride (10.6 g, 89.1 mmol) was dropwise added to ethyl α-hydroxymethylacrylate (10 g, 76.8 mmol) with ice-cooling; stirring was conducted for 30 minutes; then, a reaction was allowed to take place at 90° C. for 2 hours. After the completion of the reaction, low-boiling compounds were removed under reduced pressure to obtain unpurified ethyl α-chloromethylacrylate (11.8 g). Then, L-arabinoaminooxazoline (11.8 g, 64.0 mmol) was suspended in dimethylacetamide (80 ml). Thereto was dropwise added the ethyl α-chloromethylacrylate (11.8 g) with ice-cooling. A reaction was allowed to take place at room temperature for 4 hours. The reaction mixture was concentrated under reduced pressure to remove the solvent. To the residue was added isopropanol (100 ml), and the resulting mixture was stirred at room temperature for 1 hour. The resulting crystals were collected by filtration, washed with isopropanol (10 ml), and dried under reduced pressure to obtain a title compound (12.5 g g, 60.5%).

Analysis Results of the title compound obtained mp: 182–183° C. $^1$HNMR (DMSO-$d_6$, 400 MHz) δ ppm: 1.25 (t,3H,J=7 Hz), 3.30–3.44 (m,2H), 4.07–4.48 (m,6H), 5.22 (s,1H), 5.29 (d,1H,J=6 Hz), 5.89 (d,1H,6 Hz), 6.06 (s,1H), 6.12 (s,1H), 6.31 (s,1H), 6.97 (br,1H) IR (KBr) cm$^{-1}$: 3412, 3228, 1698, 1611, 1526, 1300, 1272, 1148, 1085, 1000, 965, 845, 648

Example 2

Production of L-2,2'-anhydro-5,6-dihydrouridine-5-exhomethylene

The L-arabinoaminooxazoline-α-chloromethylacrylic acid ester adduct (2 g, 6.20 mmol) obtained in Example 1 was dissolved in water (20 ml). Thereto were added hydroquinone (50 mg) and anhydrous sodium carbonate (0.9 g, 8.49 mmol) with ice-cooling. Stirring was conducted for 15 hours to give rise to a reaction. After the completion of the reaction, neutralization with diluted hydrochloric acid was made and the resulting mixture was concentrated to remove the solvent. The resulting residue was dissolved in methanol (20 ml). The resulting solution was dried over anhydrous magnesium sulfate, followed by concentration to remove the solvent. The resulting residue was purified by silica gel column chromatography (developing solution: chloroform/methanol) to obtain a title compound (0.187 g, 12.6%).

Analysis results of the title compound obtained
mp: 173–174° C. $^1$HNMR (DMSO-d$_6$, 400 MHz) δ ppm: 3.22–3.36 (m,2H), 3.99–4.03 (m,1H), 4.28–4.41 (m,3H), 5.00–5.08 (m,2H), 5.56–5.58 (m,1H), 5.81–5.87 (m,2H), 6.05–6.06 (m,1H) IR (KBr) cm$^{-1}$: 3427, 1619, 1492, 1449, 1405, 1311, 1154, 1088, 1059, 1025, 992, 960, 787

Example 3

Production of 2,2'-anhydro-1-(β-L-arabinofuranosyl)thymine

The L-arabinoaminooxazoline-α-chloromethylacrylic acid ester adduct (10.5 g, 32.6 mmol) obtained in Example 1 was dissolved in water (105 ml). Thereto were added hydroquinone (526 mg) and anhydrous sodium carbonate (5.18 g, 48.9 mmol) with ice-cooling. Stirring was conducted for 15 hours to give rise to a reaction. After the completion of the reaction, neutralization with acetic acid was made to obtain an aqueous solution (12.2 g, 86.9%) containing the L-2,2'-anhydro-5,6-dihydrouridine-5-exomethylene obtained in Example 2. Then, 5% palladium alumina (1.05 g) was suspended in water (52.6 g). Thereto was dropwise added the above aqueous solution at 80° C. in a hydrogen atmosphere and a reaction was allowed to take place for 1 hour. The catalyst was separated by filtration and the filtrate was concentrated to remove the solvent. The resulting residue was purified by silica gel column chromatography (developing solution: chloroform/methanol) to obtain a title compound (5.86 g, 86.6%).

Analysis results of the title compound obtained
mp: 227° C. $^1$HNMR (DMSO-d$_6$, 400 MHz) δ ppm: 1.79 (d,1H,J=1.2 Hz), 3.13–3.19 (m,1H), 3.23–3.30 (m,1H), 4.05–4.07 (m,1H), 4.37 (br,1H), 4.96 (t,1H,J=5.1 Hz), 5.17 (d,1H,J=5.6 Hz), 5.87 (d,1H,J=2.9 Hz), 6.29 (d,1H,J=5.6 Hz), 7.74 (d,1H,J=1.2 Hz) IR (KBr) cm$^{-1}$: 3407, 1668, 1618, 1556, 1492, 1378, 1268, 1240, 1158, 1095, 1061, 994, 943, 910, 800

Example 4

Production of L-3',5'-diacetyl-2'-bromothymidine 2,2'-Anhydro-1-(β-L-arabinofuranosyl)thymine (9.81 g, 40.8 mmol) was suspended in ethyl acetate (287 m) and dimethylformamide (39.6 ml). Thereto was added acetyl bromide (18.0 g, 14.6 mmol) at room temperature, and a reaction was allowed to take place at 80° C. for 1 hour. After the completion of the reaction, ethyl acetate (287 ml) and a saturated aqueous sodium hydrogencarbonate solution (100 ml) were added. Phase separation was conducted and the organic phase obtained was washed twice with a saturated aqueous sodium chloride solution (100 ml). The resulting ethyl acetate solution was dried over anhydrous sodium sulfate and concentrated to remove the solvent. To the resulting residue was added ethanol (78.5 ml), followed by stirring at room temperature for 1.5 hours. The resulting crystals were collected by filtration, washed with ethanol (16 ml) and dried under reduced pressure to obtain a title compound (12.9 g, 78.0%).

Analysis results of the title compound obtained
mp: 131° C. $^1$HNMR (DMSO-d$_6$, 400 MHz) δ ppm: 1.81 (d,3H,J=1 Hz), 2.09 (s,3H), 2.14 (s,3H), 4.24–4.34 (m,3H), 4.97–5.00 (m,1H), 5.26–5.28 (m,1H), 6.15 (d,1H,J=7.8 Hz), 7.53 (d,1H,J=1.2 Hz), 11.5 (s,1H) IR (KBr) cm$^{-1}$: 3272, 1744, 1719, 1683, 1457, 1378, 1289, 1234, 1154, 1077, 1037, 876, 805, 626, 422

Example 5

Production of L-3',5'-diacetylthymidine

L-3',5'-diacetyl-2'-bromothymidine (12.6 g, 31.2 mmol) was dissolved in methanol (332 ml). Thereto were added sodium acetate (3.16 g, 38.5 mmol) and 5% palladium alumina (1.26 g), and hydrogenation was allowed to take place at ordinary pressure at room temperature. After the completion of the reaction, the catalyst was removed by filtration and the filtrate was concentrated under reduced pressure to remove the solvent. To the resulting residue was added ethyl acetate (568 ml), followed by washing three times with a saturated aqueous sodium chloride solution (100 ml). The resulting ethyl acetate solution was dried over anhydrous sodium sulfate and concentrated to remove the solvent. To the resulting residue was added isopropanol (78.5 ml), followed by stirring at room temperature for 1.5 hours. The resulting crystals were collected by filtration, washed with ethanol (16 ml), and dried under reduced pressure to obtain a title compound (7.48 g, 73.5%).

Analysis results of the title compound obtained
mp: 125–126° C. $^1$HNMR (DMSO-d$_6$, 400 MHz) δ ppm: 1.80 (d,3H,J=0.7 Hz), 2.067 (s,3H), 2.069 (s,3H), 2.24–2.47 (m,2H), 4.13–4.27 (m,3H), 5.17–5.20 (m,1H), 6.16–6.20 (m,1H), 7.50 (d,1H,J=1.2 Hz), 11.4 (s,1H) IR (KBr) cm$^{-1}$: 3041, 1736, 1671, 1476, 1377, 1228, 1135, 1097, 1028, 952, 884, 764, 630, 563, 494, 413

Example 6

Production of L-thymidine

L-3',5'-diacetylthymidine (7.15 g, 21.9 mmol) was dissolved in methanol (36 ml). Thereto was dropwise added a 8.4 wt. % ammonia/methanol solution at room temperature. The resulting solution was subjected to a reaction at 6° C. for 3 days. After the completion of the reaction, the reaction mixture was concentrated to remove the solvent. To the resulting residue was added ethanol (21 ml), followed by stirring at room temperature for 1.5 hours. The resulting crystals were collected by filtration, washed with ethanol (3 ml) twice and dried under reduced pressure to obtain a title compound (4.95 g, 93.4%).

Analysis results of the title compound obtained
mp: 184° C. $^1$HNMR (DMSO-d$_6$, 400 MHz) δ ppm: 1.77 (d,3H,J=0.7 Hz), 2.03–2.13 (m,2H), 3.75–3.77 (m,1H), 4.22–4.26 (m,1H), 5.02–5.05 (m,1H), 5.03 (t,1H,J=5.1 Hz), 5.23 (d,1H,J=4.4 Hz), 6.17 (t,1H,J=7 Hz), 7.70 (d,1H,J=1.2 Hz), 11.3 (s,1H) IR (KBr) cm$^{-1}$: 3315, 3028, 1707, 1663, 1478, 1436, 1318, 1275, 1122, 1099, 1067, 1011, 972, 853, 628, 471

Example 7

Production of L-2,2'-anhydro-5,6-dihydrouridine

L-aminooxazoline (2.93 g, 16.9 mmol), hydroquinone (147 mg) and methyl acrylate (4.40 g, 51.0 mmol) were suspended in water (50%)-containing ethanol (30 ml). The resulting suspension was subjected to a reaction at 90° C. for 1.5 hours. After the completion of the reaction, the reaction mixture was concentrated to remove the solvent. The resulting residue was dissolved in ethanol (200 ml) and the solution was subjected to an active carbon treatment. The resulting ethanol solution was concentrated to 4 ml and allowed to stand at room temperature overnight. The resulting crystals were collected by filtration, washed with ethanol (1 ml) and dried under reduced pressure to obtain a title compound (3.74 g, 34.3%).

Analysis results of the title compound obtained mp: 177–179° C. $^1$HNMR (DMSO-d$_6$, 400 MHz) δ ppm: 2.35–2.51 (m,2H), 3.21–3.33 (m,2H), 3.46–3.60 (m,2H), 3.96–4.00 (m,1H), 4.29 (s,1H), 5.01 (s,1H), 5.05 (d,1H, J=5.6 Hz), 5.79 (s,1H), 5.85 (d,1H,J=5.6 Hz) IR (KBr) cm$^{-1}$: 3394, 2931, 1671, 1600, 1489, 1367, 1264, 1140, 1039, 944, 878, 739, 575

Example 8

Production of L-3',5'-diacetyl-2,2'-anydro-5,6-dihydrouridine

L-aminooxazoline (5.0 g, 28.7 mmol), hydroquinone (100 mg) and methyl acrylate (7.5 g, 87.0 mmol) were suspended in water (50 ml), and a reaction was allowed to take place at 50° C. for 6 hours. After the completion of the reaction, the reaction mixture was concentrated to remove the solvent. The residue was subjected to azeotropic dehydration twice using dimethylformamide (20 ml). The resulting residue was dissolved in dimethylformamide (40 ml). Thereto were added acetic anhydride (8.5 g, 83.3 mmol) and pyridine (6.8 g, 86.0 mmol), and a reaction was allowed to take place at 50° C. for 1.5 hours. After the completion of the reaction, the reaction mixture was concentrated to remove the solvent. To the resulting residue was added ethyl acetate (20 ml), followed by stirring for 1 hour with ice-cooling. The resulting crystals were collected by filtration, washed with ethyl acetate (1 ml), and dried under reduced pressure to obtain a title compound (5.2 g, 60.3%).

Analysis results of the title compound obtained mp: 150–153° C. $^1$HNMR (CDCl3-d$_6$, 400 MHz) δ ppm: 2.11 (s,3H), 2.15 (s,3H), 2.67 (t,2H,J=7 Hz), 3.59–3.73 (m,2H), 4.04–4.08 (m,1H), 4.34–4.44 (m,2H), 5.23 (d,1H, J=6 Hz), 5.33–5.34 (m, 1H), 5.86 (d, 1H, J=6 Hz) IR (KBr) cm$^{-1}$: 3440, 1746, 1688, 1606, 1485, 1460, 1366, 1232, 1134, 1098, 1049, 992, 734

Example 9

Production of L-3',5'-di-p-chlorobenzoyl-2,2'-anhydro-5,6-dihydrouridine

L-aminooxazoline (5.0 g, 28.7 mmol), hydroquinone (100 mg) and methyl acrylate (7.5 g, 87.0 mmol) were suspended in water (50 ml). A reaction was allowed to take place at 50° C. for 6 hours. After the completion of the reaction, the reaction mixture was concentrated to remove the solvent. The concentrate was subjected to azeotropic dehydration twice using dimethylformamide (20 ml). The resulting residue was dissolved in pyridine (60 ml). Thereto was added p-chlorobenzoic acid chloride (11.1 g, 62.9 mmol) with ice-cooling. A reaction was allowed to take pace at room temperature for 2 hours. After the completion of the reaction, water (60 ml) was added and stirring was conducted at room temperature for 1 hour. The resulting crystals were collected by filtration, washed with methanol (10 ml), and dried under reduced pressure to obtain a title compound (10.2 g, 70.3%).

Analysis results of the title compound obtained mp: 178–180° C. $^1$HNMR (DMSO-d$_6$, 400 MHz) δ ppm: 2.39–2.52 (m,2H), 3.51–3.66 (m,2H), 4.41–4.42 (m,2H), 4.78–4.79 (m,1H), 5.63–5.64 (m,2H), 6.02–6.04 (m,1H), 7.56–7.66 (m,4H), 7.93–8.04 (m,4H) IR (KBr) cm$^{-1}$: 3435, 1726, 1594, 1488, 1455, 1403, 1364, 1274, 1093, 1043, 1016, 850, 760

Example 10

Production of L-3',5'-diacetyl-2'-bromo-5,6-dihydrouridine

L-3',5'-diacetyl-2,2'-anhydro-5,6-dihydrouridine (25.7 g, 85.6 mmol) was suspended in ethyl acetate (200 ml) and dimethylformamide (50 ml). Thereto was added 30% hydrogen bromide acetic acid (33.9 g, 125 mmol) at room temperature. A reaction was allowed to take place at 80° C. for 1 hour. After the completion of the reaction, ethyl acetate (200 ml) was added. The resulting mixture was washed with water (50 ml) and a saturated aqueous sodium hydrogencarbonate solution (25 ml) twice. The resulting ethyl acetate solution was dried over anhydrous sodium sulfate and then concentrated under reduced pressure to remove the solvent. To the residue were added ethanol (20 ml) and hexane (20 ml), followed by stirring at room temperature for 1 hour. The resulting crystals were collected by filtration, washed with an ethanol/hexane mixed solvent (1:1, 10 ml), and dried under reduced pressure to obtain a title compound (26.5 g, 81.2%).

Analysis results of the title compound obtained mp: 109–112° C. $^1$HNMR (DMSO-d$_6$, 400 MHz) δ ppm: 2.06 (s,3H), 2.14 (s,3H), 2.58 (t,2H,J=7 Hz), 3.31–3.61 (m,2H), 4.14–4.23 (m,3H), 4.80–4.84 (m,1H), 5.18–5.20 (m,1H), 6.05 (d,1H,J=9 Hz), 10.5 (s,1H) IR (KBr) cm$^{-1}$: 3448, 1742, 1655, 1484, 1449, 1379, 1228, 1078, 1024

Example 11

Production of L-3',5'-di-p-chlorobenzoyl-2'-bromo-5,6-dihydrouridine

L-3',5'-di-p-chlorobenzoyl-2,2'-anhydro-5,6-dihydrouridine (17.2 g, 34.0 mmol) was suspended in ethyl acetate (120 ml) and dimethylformamide (30 ml). Thereto was dropwise added 30% hydrogen bromide acetic acid (14.0 g, 51.9 mmol) at room temperature. A reaction was allowed to take place for 5 hours. After the completion of the reaction, the reaction mixture was washed with water (50 ml) and a saturated aqueous sodium hydrogencarbonate solution (25 ml) twice. The resulting ethyl acetate solution was dried over anhydrous sodium sulfate and then concentrated under reduced pressure to remove the solvent. The resulting residue was purified by silica gel column chromatography (developing solution: ethyl acetate/hexane) to obtain a title compound (13.3 g, 66.7%).

Analysis results of the title compound obtained mp: 148–149° C. $^1$HNMR (DMSO-$d_6$, 400 MHz) δ ppm: 2.55–2.59 (m,2H), 3.41–3.47 (m,2H), 4.55–4.57 (m,3H), 5.02–5.05 (m,1H), 5.56–5.58 (m,1H), 6.21 (d,1H,J=8 Hz), 7.61–7.69 (m,4H), 7.99–8.07 (m,4H), 10.52 (s,1H) IR (KBr) cm$^{-1}$: 3242, 1728, 1594, 1488, 1446, 1402, 1373, 1271, 1093, 1015, 850, 757, 685, 529

Example 12

Production of L-3',5'-diacetyl-2'-deoxy-5,6-dihydrouridine

L-3',5'-diacetyl-2'-bromo-5,6-dihydrouridine (10 g, 26.2 mmol) was dissolved in water (50%)-containing methanol (150 ml). Thereto were added sodium acetate (6.3 g, 76.8 mmol) and 5% palladium barium sulfate (2.5 g), and hydrogenation was conducted at ordinary pressure at room temperature. After the completion of the reaction, the catalyst was removed by filtration and the filtrate was concentrated under reduced pressure to remove the solvent. The residue was dissolved in ethyl acetate (200 ml). The resulting solution was washed with a saturated aqueous sodium hydrogencarbonate solution (50 ml) and a saturated aqueous sodium chloride solution (50 ml). The resulting ethyl acetate solution was dried over anhydrous sodium sulfate and concentrated under reduced pressure to remove the solvent to obtain a title compound (7.3 g, 88.7%).

Analysis results of the title compound obtained $^1$HNMR (DMSO-$d_6$, 400 MHz) δ ppm: 1.99–2.06 (m,1H), 2.30–2.32 (m,1H), 2.50–2.89 (m,2H), 3.31–3.36 (m,2H), 4.02–4.04 (m,1H), 4.10–4.18 (m,2H), 5.07–5.10 (m,1H), 6.11–6.15 (m,1H), 10.3 (s,1H) IR (KBr) cm$^{-1}$: 2974, 1718, 1488, 1449, 1374, 1241, 1048, 881, 762

Example 13

Production of L-2'-deoxy-5,6-dihydrouridine

3',5'-Diacetyl-2'-deoxy-L-5,6-dihydrouridine (7.0 g, 22.3 mmol) was dissolved in methanol (10 ml). Thereto was added a 2.0 N ammonia/methanol solution (75 ml, 150 mmol) with ice-cooling. The mixture was allowed to stand at room temperature overnight, followed by concentration to remove the solvent. The resulting residue was dissolved in a small amount of methanol. Thereto were added isopropyl alcohol and isopropyl ether, followed by stirring for 1 hour. The resulting crystals were collected by filtration, washed with a methanol/isopropyl ether mixed solvent (1 ml), and dried under reduced pressure to obtain a title compound (3.95 g, 65.5%).

Analysis results of the title compound obtained mp: 136–138° C. $^1$HNMR (DMSO-$d_6$, 400 MHz) δ ppm: 1.77–1.82 (m,1H), 2.00–2.05 (m,1H), 2.48–2.52 (m,2H), 3.29–3.45 (m,4H), 3.59–3.62 (m,1H), 4.10–4.13 (m,1H), 4.76–4.79 (m,1H), 5.12 (d,1H,J=4 Hz), 6.08–6.12 (m,1H), 10.20 (s,1H) IR (KBr) cm$^{-1}$: 3412, 2920, 1696, 1484, 1443, 1370, 1286, 1214, 1091, 1056

Example 14

Production of L-3',5'-di-p-chlorobenzoyl-2'-deoxy-5,6-dihydrouridine

L-2'-deoxy-5,6-dihydrouridine (0.5 g, 2.17 mmol) was dissolved in pyridine (2.5 ml). Thereto was added p-chlorobenzoic acid chloride (0.80 g, 4.56 mmol) with ice-cooling. A reaction was allowed to take place at room temperature for 0.5 hour. After the completion of the reaction, water (3 ml) was added, followed by stirring at room temperature for 0.5 hour. The resulting crystals were collected by filtration, washed with an ethyl acetate/hexane mixed solvent (10 ml), and dried under reduced pressure to obtain a title compound (0.93 g, 85.0%).

Analysis results of the title compound obtained mp: 184–185° C. $^1$HNMR (DMSO-$d_6$, 400 MHz) δ ppm: 2.23–2.29 (m,1H), 2.43–2.58 (m,3H), 3.36–3.42 (m,2H), 4.36–4.38 (m,1H), 4.50–4.53 (m,2H), 5.48–5.51 (m,1H), 6.24–6.28 (m,1H), 7.42–7.64 (m,4H), 7.98–8.03 (m,4H), 10.3 (s,1H) IR (KBr) cm$^{-1}$: 3430, 1721, 1594, 1488, 1448, 1402, 1374, 1276, 1220, 1175, 1093, 1015, 852, 761, 687, 529

Example 15

Production of L-3,5-di-p-chlorobenzoyl-2-deoxy-ribose

L-3',5'-di-p-chlorobenzoyl-2'-deoxy-5,6-dihydrouridine (1.56 g, 3.26 mmol) was dissolved in dioxane (18 ml) at 50° C. Thereto was dropwise added an aqueous solution (3.3 ml) of p-toluenesulfonic acid (4.35 g, 22.9 mmol). A reaction was allowed to take place at 50° C. for 6.5 hours. The reaction mixture was neutralized with a saturated aqueous sodium hydrogencarbonate solution and extracted with ethyl acetate (30 ml). The organic phase obtained was washed with a saturated aqueous sodium chloride solution, dried over anhydrous sodium sulfate, and concentrated to remove the solvent to obtain a title compound (0.88 g, 65.4%).

Analysis results of the title compound obtained $^1$HNMR (DMSO-$d_6$, 400 MHz) δ ppm: 1.96–2.52 (m,2H), 4.36–4.54 (m,3H), 5.34–5.60 (m,2H), 6.45 (d,1H, J=4.1 Hz,1-OH), 6.69 (d,1H,J=5.1 Hz,1-OH), 7.59–7.63 (m,4H), 7.95–8.01 (m,4H)

Example 16

Production of L-3,5-di-p-chlorobenzoyl-2-deoxy-ribose-1-methyl Ether

L-3,5-di-p-chlorobenzoyl-2-deoxy-ribose (0.88 g, 2.17 mmol) was dissolved in methanol (4.2 ml). Thereto was added a 4N hydrochloric acid/dioxane solution (0.03 ml). A reaction was allowed to take place at room temperature for 12 hours. Seed crystals were added with ice-cooling, followed by stirring for 1 hour. The resulting crystals were collected by filtration, washed with a small amount of methanol, and dried under reduced pressure to obtain a title compound (0.42 g, 49.2%).

Analysis results of the title compound obtained mp: 173–174° C. $^1$HNMR (DMSO-$d_6$, 400 MHz) δ ppm: 2.18–2.39 (m,1H), 2.51–2.55 (m,1H), 3.36 (s,3H,1-OMe), 3.43 (s,3H,1-OMe), 4.51–4.64 (m,3H), 5.19–5.24 (m,1H), 5.39–5.62 (m,1H), 7.39–7.44 (m,4H), 7.94–8.04 (m,4H) IR (KBr) cm$^{-1}$: 1724, 1594, 1489, 1403, 1275, 1204, 1176, 1123, 1015, 936, 860, 761, 686, 528

Example 17

Production of
L-3,5-di-p-chlorobenzoyl-2-deoxy-ribose-1-methyl Ether

L-3',5'-di-p-chlorobenzoyl-2'-deoxy-5,6-dihydrouridine (0.5 g, 0.99 mmol) was dissolved in dioxane (5.0 ml) at 50° C. Thereto were dropwise added water (0.018 g) and methanesulfonic acid (209 mg, 2.17 mmol) dissolved in methanol (2 ml), followed by stirring for 32 hours. The reaction mixture was neutralized with a saturated aqueous sodium hydrogencarbonate solution and then concentrated to remove the solvent. To the residue was added water (5 ml), followed by extraction with ethyl acetate (10 ml). The organic phase obtained was dried over anhydrous sodium sulfate and concentrated to remove the solvent. The residue was purified by silica gel column chromatography (developing solution: ethyl acetate/hexane) to obtain a title compound (0.148 g, 35.3%).

The NMR and IR spectrum of the compound were the same as those of Example 16.

Example 18

Production of L-2-deoxy-ribse

L-3', 5'-diacetyl-2'-deoxy-5,6-dihydrouridine (0.51 g, 1.64 mmol) was dissolved in water (3 ml). Thereto was added sodium hydroxide (0.3 g, 7.5 mmol). A reaction was allowed to take place at room temperature for 1 hour. After the completion of the reaction, Amberlite 120H$^+$ (an acidic resin)(3 g) was added, followed by stirring for 10 minutes. The resin was separated by filtration. To the filtrate (aqueous solution) was dropwise added concentrated hydrochloric acid (0.17 g, 1.59 mmol) with ice-cooling, and a reaction was allowed to take place at room temperature for 5 hours. After the completion of the reaction, Amberlite 400 (a basic resin) (3 g) was added, followed by stirring for 10 minutes. The resin was separated by filtration and the filtrate was concentrated to remove water to obtain a title compound (0.10 g, 47.4%). The 2-deoxy-L-ribose (0.1 g, 0.75 mmol) was dissolved in methanol (1.2 ml). Thereto was added aniline (0.47 g, 5.0 mmol), followed by stirring for 3 hours with ice-cooling. The resulting crystals were collected by filtration, washed with a small amount of a cold methanol/isopropanol mixed solvent and dried under reduced pressure to obtain L-2-deoxy-N-phenyl-erythro-pentofuranosylamine (0.14 g, 90%). Confirmation of structure was made using the derivative.

L-2-deoxy-N-phenyl-erythro-pentofuranosylamine
mp: 168° C. $^1$HNMR (DMSO-d$_6$, 90 MHz) δ ppm: 1.65–1.92 (m,2H), 3.41–3.82 (m,4H), 4.30–4.78 (m,3H), 6.24–6.75 (m,3H), 6.95–7.15 (m,2H) IR (KBr) cm$^{-1}$: 3333, 3267, 2900, 1605, 1532, 1499, 1445, 1378, 1343, 1309, 1259, 1175, 1151, 1087, 1067, 999, 973, 892, 829, 758, 723, 694

INDUSTRIAL APPLICABILITY

In the present invention have been found a novel process for producing 2,2'-anhydro-1-(62 -L-arabinofuranosyl) thymine which is a novel and useful synthesis intermediate; a novel process for producing L-thymidine from the 2,2'-anhydro-1-(β-L-arabinofuranosyl)thymine; and a novel process for producing a L-2'-deoxyribose derivative (a useful synthesis intermediate) via a L-2,2'-anhydro-5,6-dihydrocyclouridine derivative. Thereby, synthesis of a variety of L-nucleic acid derivatives which has been difficult, has become possible.

What is claimed is:

1. A process for producing L-thymidine comprising:
   (a) a step of reacting L-arabinoaminooxazoline represented by the following formula (1)

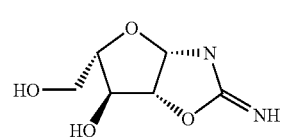

with an acrylic acid derivative represented by the following formula (2)

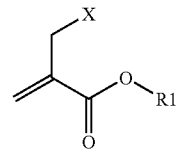

(wherein R1 is a lower alkyl group, and X is chlorine, a p-toluenesulfonyloxy group or a methanesulfonyloxy group) to synthesize a L-arabinoaminooxazoline derivative represented by the following formula (3)

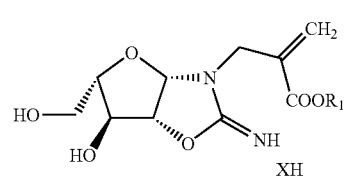

(wherein X and R1 have the same definitions as given above), (b) a step of reacting a base with the L-arabinoaminooxazoline derivative represented by the formula (3) to synthesize a L-2,2 anhydronucleic acid derivative represented by the following formula (4)

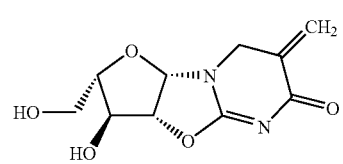

(c) a step of isomerizing the L-2,2 anhydronucleic acid derivative represented by the formula (4) to synthesize 2,2 anhydro-1-((-L-arabinofuranosyl)thymine represented by the following formula (5)

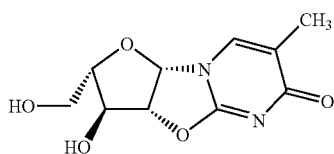
(5)

(d) a step of subjecting the 2,2 anhydro-1-((-L-arabino-furanosyl)thymine represented by the formula (5) to halogenation and subsequent protection, or protection and subsequent halogenation, or protection and simultaneous halogenation to synthesize a 2 position-halogenated L-thymidine derivative represented by the following formula (6)

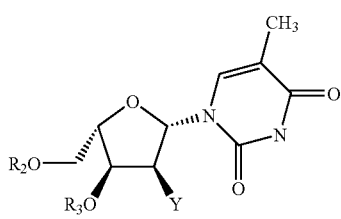
(6)

(wherein R2 and R3 are each independently a protecting group for hydroxyl group, and Y is a halogen atom), (e) a step of dehalogenation of the compound represented by the formula (6) to synthesize a L-thymidine derivative represented by the following formula (7)

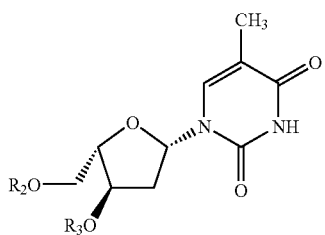
(7)

(wherein R2 and R3 have the same definitions as given above), and (f) a step of deblocking the compound represented by the formula (7) to synthesize L-thymidine.

2. A process for producing 2,2 anhydro-1-((-L-arabinofuranosyl)thymine comprising:

(a) a step of reacting L-arabinoaminooxazoline represented by the following formula (1)

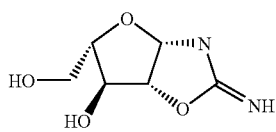
(1)

with an acrylic acid derivative represented by the following formula (2)

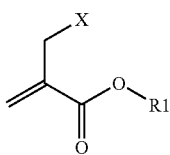
(2)

(wherein R1 is a lower alkyl group and X is chlorine, a p-toluenesulfonyloxy group or a methanesulfonyloxy group) to synthesize a L-arabinoaminooxazoline derivative represented by the following formula (3)

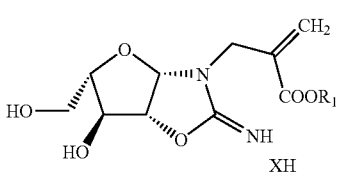
(3)

(wherein X and R1 have the same definitions as given above), (b) a step of allowing a base to act on the L-arabinoaminooxazoline derivative represented by the formula (3) to synthesize a L-2,2 anhydronucleic acid derivative represented by the following formula (4)

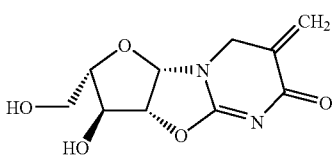
(4)

and (c) a step of isomerizing the a L-2,2 anhydronucleic acid derivative represented by the formula (4) to synthesize 2,2 anhydro-1-((-L-arabinofuranosyl)thymine represented by the following formula (5).

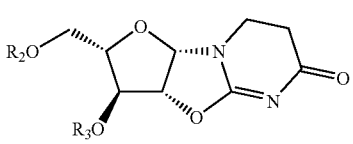
(9)

3. A process for producing a L-arabinoaminooxazoline derivative comprising:

a step of reacting L-arabinoaminooxazoline represented by the following formula (1)

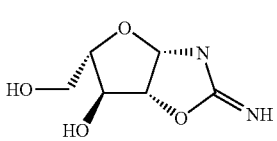
(1)

with an acrylic acid derivative represented by the following formula (2)

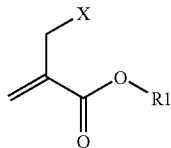
(2)

(wherein R1 is a lower alkyl group, and X is chlorine, a p-toluenesulfonyloxy group or a methanesulfonyloxy group) to synthesize a L-arabinoaminooxazoline derivative represented by the following formula (3)

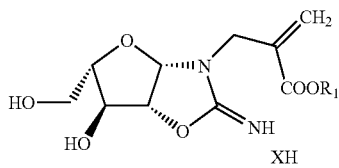
(3)

(wherein X and R1 have the same definitions as given above).

4. A L-arabinoaminooxazoline derivative represented by the following formula (3)

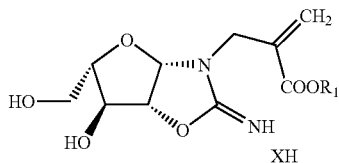
(3)

(wherein R1 is a lower alkyl group, and X is chlorine, a p-toluenesulfonyloxy group or a methanesulfonyloxy group).

5. A process for producing a L-2,2 anhydronucleic acid derivative comprising allowing a base to act on a L-arabinoaminooxazoline derivative represented by the following formula (3)

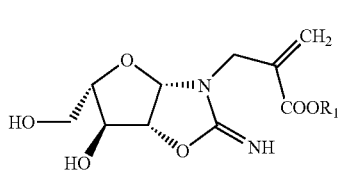
(3)

(wherein R1 is a lower alkyl group and X is chlorine, a p-toluenesulfonyloxy group or a methanesulfonyloxy group) to synthesize a L-2,2 anhydronucleic acid derivative represented by the following formula (4)

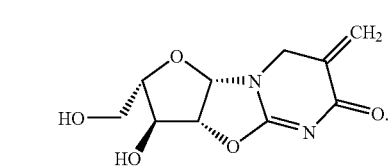
(4)

6. A L-2,2 anhydronucleic acid derivative represented by the following formula (4)

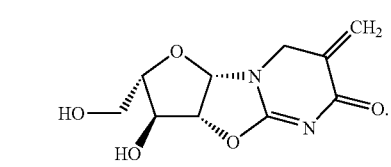
(4)

7. A process for producing 2,2 anhydro-1-((-L-arabinofuranosyl)thymine comprising isomerizing a L-2,2 anhydronucleic acid derivative represented by the following formula (4)

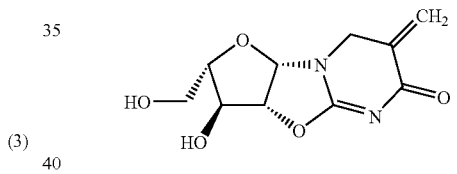
(4)

to synthesize 2,2 anhydro-1-((-L-arabinofuranosyl)thymine represented by the following formula (5)

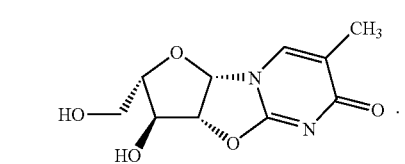
(5)

8. 2,2 Anhydro-1-((-L-arabinofuranosyl)thymine represented by the following formula (5)

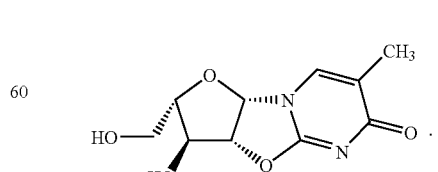
(5)

9. A process for producing a 2 position-halogenated L-thymidine derivative comprising subjecting 2,2 anhydro- 1-((-L-arabinofuranosyl)thymine represented by the following formula (5)

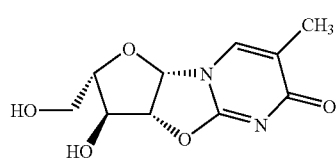
(5)

to halogenation and subsequent protection, or protection and subsequent halogenation, or protection and simultaneous halogenation to synthesize a 2 position-halogenated L-thymidine derivative represented by the following formula (6)

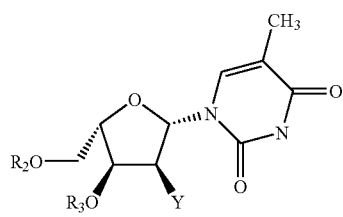
(6)

(wherein R2 and R3 are each independently a protecting group for hydroxyl group, and Y is a halogen atom).

10. A 2 position-halogenated L-thymidine derivative represented by the following formula (6)

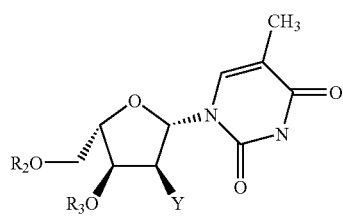
(6)

(wherein R2 and R3 are each independently a protecting group for hydroxyl group, and Y is a halogen atom).

11. A process for producing a L-thymidine derivative comprising subjecting a compound represented by the following formula (6)

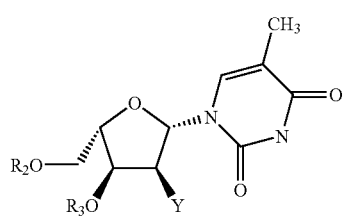
(6)

(wherein R2 and R3 are each independently a protecting group for hydroxyl group, and Y is a halogen atom) to dehalogenation to synthesize a L-thymidine derivative represented by the following formula (7)

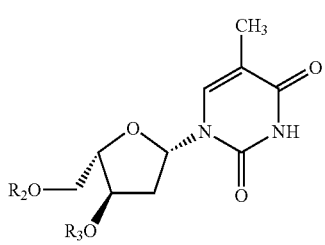
(7)

(wherein R2 and R3 have the same definitions as given above).

12. A process for producing a L-2-deoxyribose derivative, comprising:

I. a step of reacting L-arabinoaminooxazoline represented by the following formula (1)

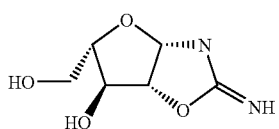
(1)

with a lower alkyl acrylic acid ester to synthesize L-2,2 anhydro-1-((-arabinofuranosyl)-5,6-dihydrouridine represented by the following formula (8)

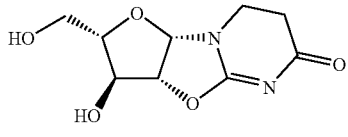
(8)

II. a step of protection of the L-2,2 anhydro-1-((-arabinofuranosyl)-5,6-dihydrouridine represented by the formula (8) to synthesize a L-2,2 anhydro-5,6-dihydrouridine derivative represented by the following formula (9)

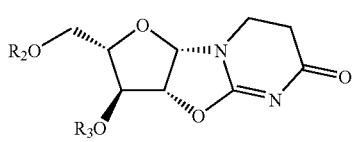
(9)

(wherein R2 and R3 are each independently a protecting group for hydroxyl group), III. a step of halogenation of the L-2,2 anhydro-5,6-dihydrouridine derivative represented by the formula (9) to synthesize a 2 position-halogenated L-5,6-dihydrouridine derivative represented by the following formula (10)

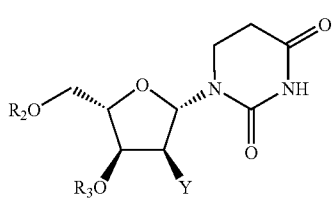

(10)

(wherein R2, R3 and Y have the same definitions as given above),

IV. a step of subjecting the compound represented by the formula (10) to dehalogenation, or dehalogenation and subsequent deblocking, or deblocking and subsequent dehalogenation, or deblocking and simultaneous dehalogenation to synthesize a L-2 deoxy-5,6-dihydrouridine derivative represented by the following formula (11)

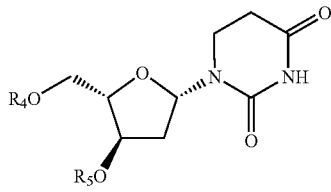

(11)

(wherein R4 and R5 are each independently a hydrogen atom or a protecting group for hydroxyl group), and V. a step of a decomposition reaction of the compound represented by the formula (11) to obtain a L-2-deoxyribose derivative represented by the following formula (12)

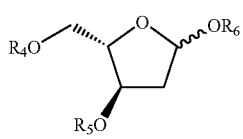

(12)

wherein R4 and R5 have the same definitions as given above, and R6 is hydrogen, a methyl group or an ethyl group).

13. A process for producing a L-2,2 anhydro-5,6-dihydrouridine derivative comprising:

I. a step of reacting L-arabinoaminooxazoline represented by the following formula (1)

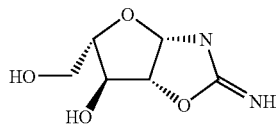

(1)

with a lower alkyl acrylic acid ester to synthesize L-2,2 anhydro-1-((-arabinofuranosyl)-5,6-dihydrouridine represented by the following formula (8)

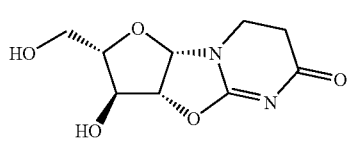

(8)

and

II. a step of subjecting the compound represented by the formula (8) to protection to synthesize a L-2,2 anhydro-5,6-dihydrouridine derivative represented by the following formula (9)

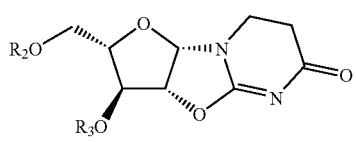

(9)

(wherein R2 and R3 are each independently a protecting group for hydroxyl group).

14. A L-2,2 anhydro-5,6-dihydrouridine derivative represented by the following formula (9)

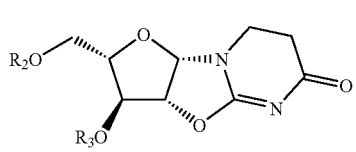

(9)

(wherein R2 and R3 are each independently a protecting group for hydroxyl group).

15. A process for producing a 2 position-halogenated L-5,6-dihydrouridine derivative comprising halogenating a compound represented by the following formula (9)

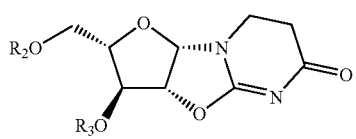

(9)

(wherein R2 and R3 are each independently a protecting group for hydroxyl group) to synthesize a 2 position-halogenated L-5,6-dihydrouridine derivative represented by the following formula (10)

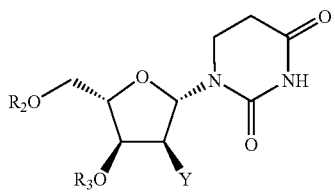
(10)

(wherein R2, R3 have the same definition as given above and Y is a halogen atom).

16. A process for producing a L-2 deoxy-5,6-dihydrouridine derivative comprising subjecting a compound represented by the following formula (10)

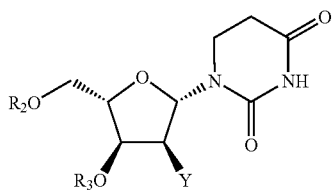
(10)

(wherein R2 and R3 are each independently a protecting group for hydroxyl group and Y is a halogen atom) to dehalogenation, or dehalogenation and subsequent deblocking, or deblocking and subsequent dehalogenation, or deblocking and simultaneous dehalogenation to synthesize a L-2 deoxy-5,6-dihydrouridine derivative represented by the following formula (11)

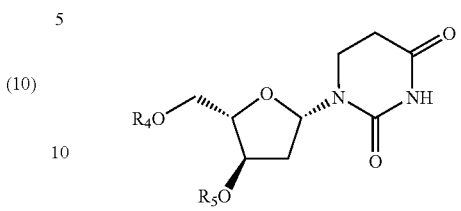
(11)

(wherein R4 and R5 are each independently a hydrogen atom or a protecting group for hydroxyl group).

17. A process for producing a L-2-deoxyribose derivative comprising decomposing a L-2 deoxy-5,6-dihydrouridine derivative represented by the following formula (11)

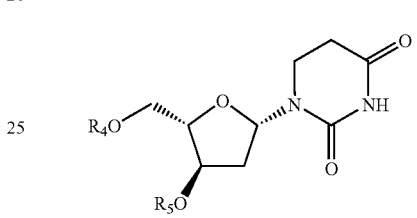
(11)

(wherein R4 and R5 are each independently a hydrogen atom or a protecting group for hydroxyl group) to obtain a L-2-deoxyribose derivative represented by the following formula (12)

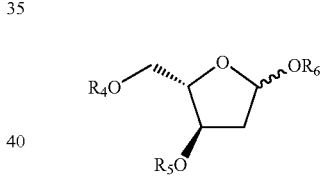
(12)

(wherein R4 and R5 have the same definitions as given above, and R6 is hydrogen, a methyl group or an ethyl group).

* * * * *